US 12,109,385 B2

(12) United States Patent
Hoell, Jr. et al.

(10) Patent No.: US 12,109,385 B2
(45) Date of Patent: Oct. 8, 2024

(54) LINE HOLDER

(71) Applicant: NxStage Medical, Inc., Lawrence, MA (US)

(72) Inventors: Joseph A. Hoell, Jr., Dunbarton, NH (US); Eric Zoglio, Derry, NH (US); M. Dominika Kulinski, Middleton, MA (US); Kenneth E. Buckler, Methuen, MA (US)

(73) Assignee: NxStage Medical, Inc., Lawrence, MA (US)

( * ) Notice: Subject to any disclaimer, the term of this patent is extended or adjusted under 35 U.S.C. 154(b) by 434 days.

(21) Appl. No.: 17/602,680

(22) PCT Filed: Apr. 9, 2020

(86) PCT No.: PCT/US2020/027407
§ 371 (c)(1),
(2) Date: Oct. 8, 2021

(87) PCT Pub. No.: WO2020/210447
PCT Pub. Date: Oct. 15, 2020

(65) Prior Publication Data

US 2022/0161014 A1 May 26, 2022

(51) Int. Cl.
*A61M 1/28* (2006.01)
*A61M 39/08* (2006.01)
(Continued)

(52) U.S. Cl.
CPC ........... *A61M 39/08* (2013.01); *B23Q 3/1546* (2013.01); *H01F 7/0263* (2013.01); *A61M 1/28* (2013.01)

(58) Field of Classification Search
CPC ........ A61M 39/08; A61M 1/28; A61M 1/367; A61M 5/1418; A61M 2209/082;
(Continued)

(56) References Cited

U.S. PATENT DOCUMENTS 4,944,311 A 7/1990 Eldridge, Jr. et al.
6,460,592 B1 * 10/2002 Sano .................... B29C 66/8167
156/304.2
(Continued)

FOREIGN PATENT DOCUMENTS

AU 2006249279 A1 1/2007
DE 202014008927 U1 12/2014
GB 2541082 A * 2/2017 ............ A61M 16/04

OTHER PUBLICATIONS

International Search Report and Written Opinion mailed Jul. 16, 2020 for International Patent Application No. PCT/US2020/027407.

*Primary Examiner* — Joseph W Drodge
(74) *Attorney, Agent, or Firm* — Potomac Law Group, PLLC

(57) ABSTRACT

A line mount includes a treatment machine having a housing and one or more magnets or ferromagnetic elements mounted thereon, a line holder having at least one complementary one of magnets and ferromagnetic elements such as to cause the line holder to be attachable magnetically to the housing. The one or more magnets or ferromagnetic elements being numbered and arranged to permit the line holder to be supported thereby in multiple positions and orientations relative to the housing.

16 Claims, 5 Drawing Sheets

(51) Int. Cl.
*B23Q 3/15* (2006.01)
*B23Q 3/154* (2006.01)
*B25B 1/00* (2006.01)
*H01F 7/02* (2006.01)

(58) Field of Classification Search
CPC ........ A61M 1/14; A61M 39/10; A61M 39/12; H01F 7/0263; B23Q 3/15; B23Q 3/154; B23Q 3/1546; B25B 11/002
See application file for complete search history.

(56) References Cited

U.S. PATENT DOCUMENTS

| | | |
|---|---|---|
| 10,569,055 B1* | 2/2020 | Sigsworth ............. F16L 3/2235 |
| 2010/0096571 A1* | 4/2010 | Webster ................ F16K 31/086 |
| | | 251/65 |
| 2014/0031736 A1* | 1/2014 | Wright .................. A61M 1/367 |
| | | 604/500 |
| 2014/0375186 A1 | 12/2014 | Tarnow et al. |
| 2016/0296726 A1 | 10/2016 | Mallach |
| 2017/0173521 A1* | 6/2017 | Dickinson ............. B01D 53/32 |
| 2018/0236155 A1 | 8/2018 | Wieskotten et al. |
| 2020/0086107 A1* | 3/2020 | Ruffolo ................ A61J 15/003 |

\* cited by examiner

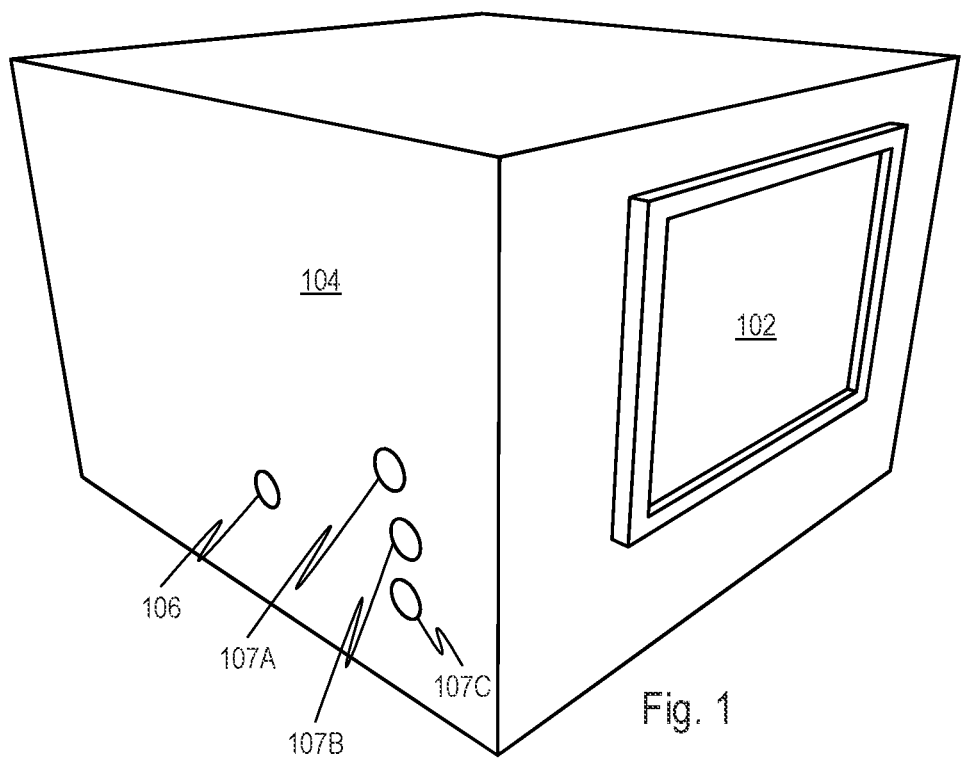
Fig. 1
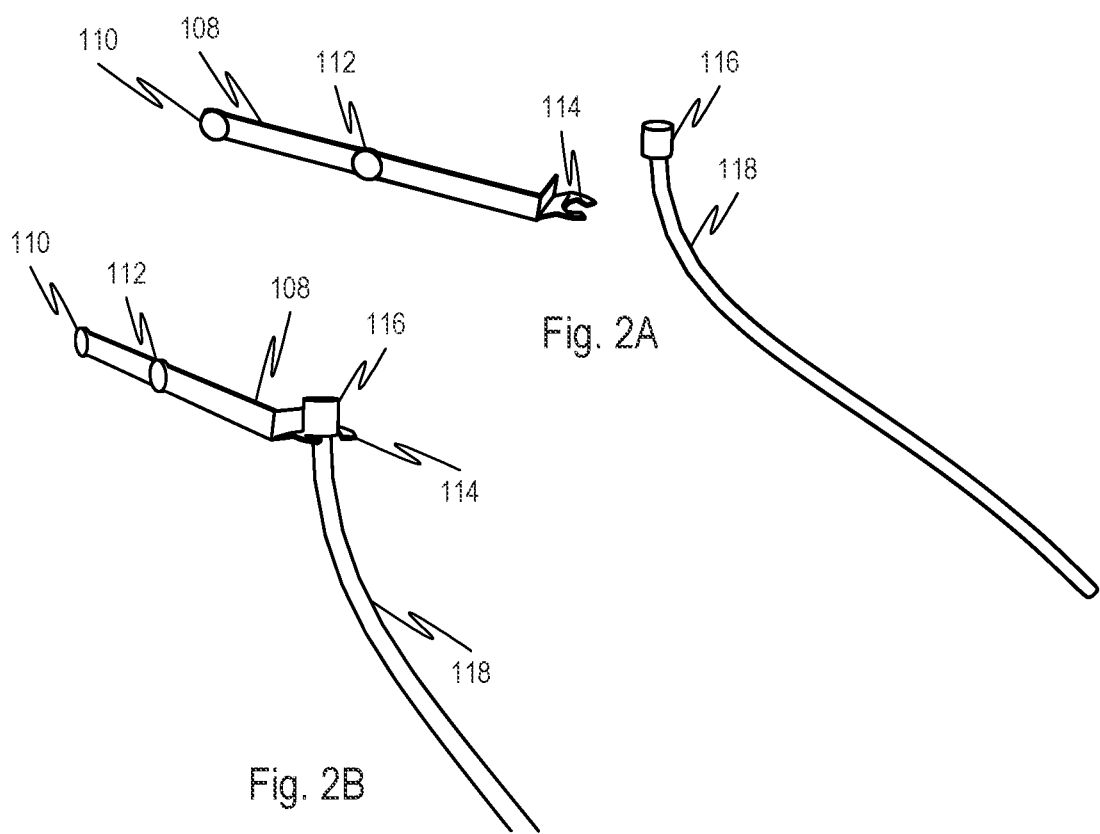
Fig. 2A
Fig. 2B

LINE HOLDER

CROSS-REFERENCE TO RELATED APPLICATIONS

This Application is a U.S. national stage filing under 35 U.S.C. § 371 of International Application No. PCT/US2020/027407, filed Apr. 9, 2020, which claims priority to and the benefit of U.S. Provisional Patent Application No. 62/831,291 filed Apr. 9, 2019 and U.S. Provisional Patent Application No. 62/938,976 filed Nov. 22, 2019, all of which are hereby incorporated by reference in their entireties.

BACKGROUND

The present invention relates to a medical treatment machine that provides a mounting fixture for lines such as patient fluid lines of a dialysis machine and more particularly, in embodiments, to peritoneal dialysis machines that provide such fixtures for a fill/drain line for performing dialysis.

Peritoneal dialysis machines have mounting fixtures that function as an extra hand and facilitate the maintenance of sterile conditions by helping operators avoid contacting the tips of sterile lines, including attached connectors, with non-sterile surfaces. Such devices, known as organizers, allow for single-handed manipulation by a user.

In a prior art organizer, a mount (support that holds the fluid line) pivots on a stationary support. The mount is permitted to pivot downwardly upon the application of a sufficient force to the mount to avoid excessive torque being applied which can damage the housing of the peritoneal dialysis device. In this regard, the mount can pivot on a hinge but magnets prevent the pivoting until the breakaway torque is applied at which points the magnets separate and the mount pivots downwardly. In this way, excessive forces are avoided.

SUMMARY

A device allows for the maintenance of sterile handling of fluid lines while providing flexibility to position the device in a variety of angles and positions for convenience. In embodiments, the device includes a mount that magnetically attaches to a treatment machine housing in a variety of positions and orientations. In further embodiments, a ferromagnetic collar or magnet is affixed to a line and attaches easily to a magnet attached to a treatment machine housing in a variety of positions and orientations.

As used herein, a ferromagnetic element is one that is attracted to a magnet such as iron or steel or a magnet.

The present Objects and advantages of embodiments of the disclosed subject matter will become apparent from the following description when considered in conjunction with the accompanying drawings.

BRIEF DESCRIPTION OF DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

FIG. 1 shows a treatment machine housing with a display according to embodiments of the disclosed subject matter.

FIGS. 2A and 2B show a mount with a treatment line separated and engaged according to embodiments of the disclosed subject matter.

DETAILED DESCRIPTION

FIG. 1 shows a treatment machine housing 104 with a display 102 according to embodiments of the disclosed subject matter. FIGS. 2A and 2B show a mount 114 with a treatment line 118 separated (FIG. 2A) and engaged with the mount 114 (FIG. 2B) according to embodiments of the disclosed subject matter. The way the mount 114 is attached to the housing 104 is illustrated in the following figures.

Figure 3A:
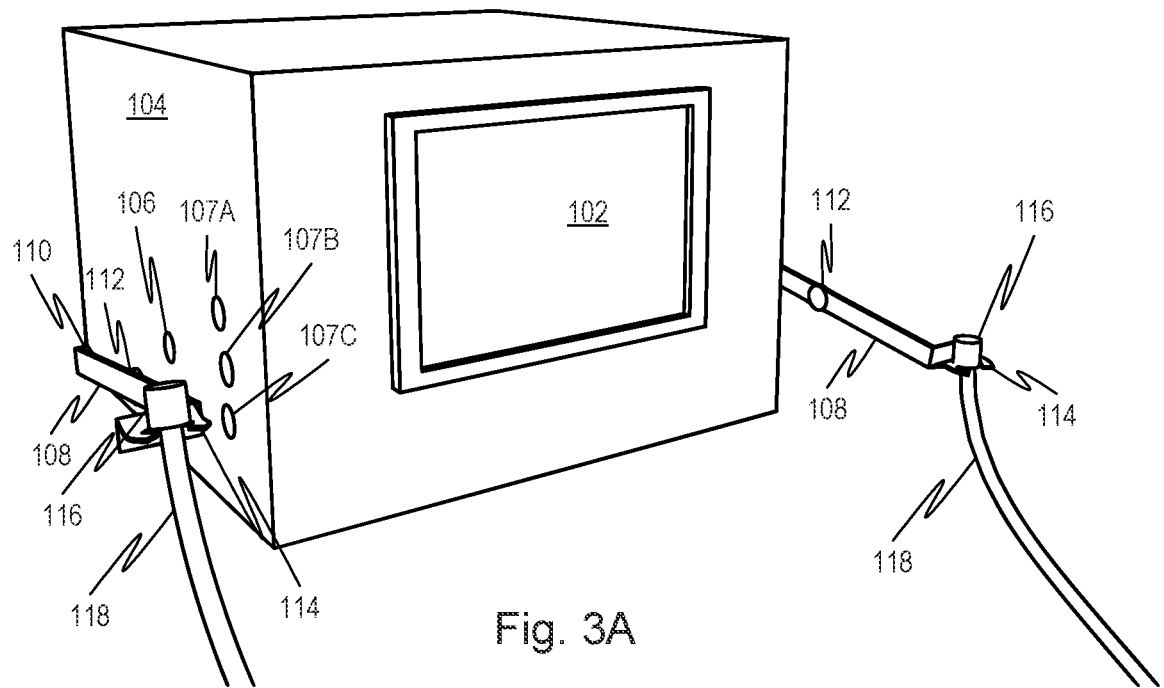
FIGS. 3A and 3B show a treatment machine housing with mounts ready to attach to the housing and attached, respectively, according to embodiments of the disclosed subject matter.
Figure 3B:
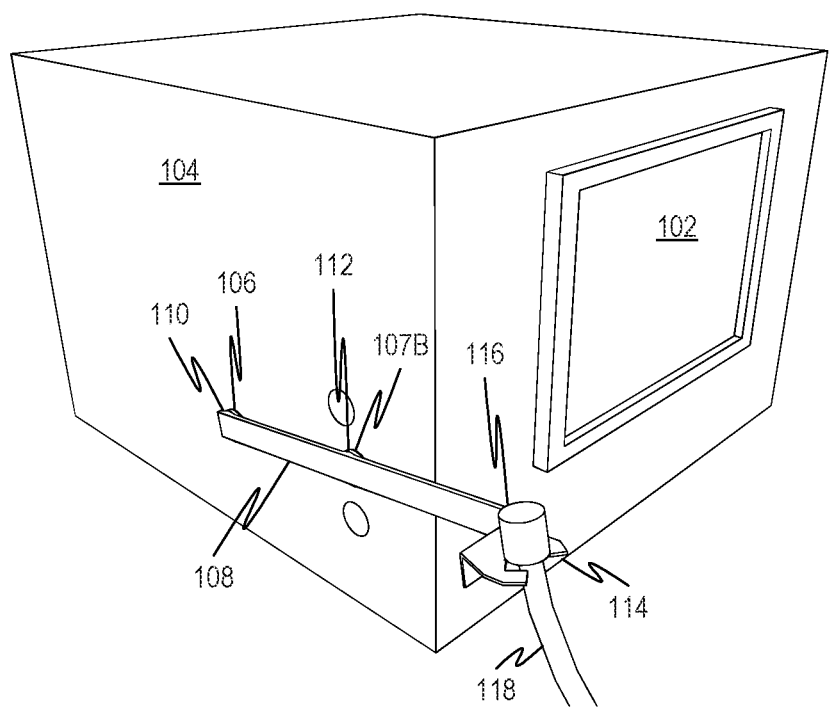
Figure 4:
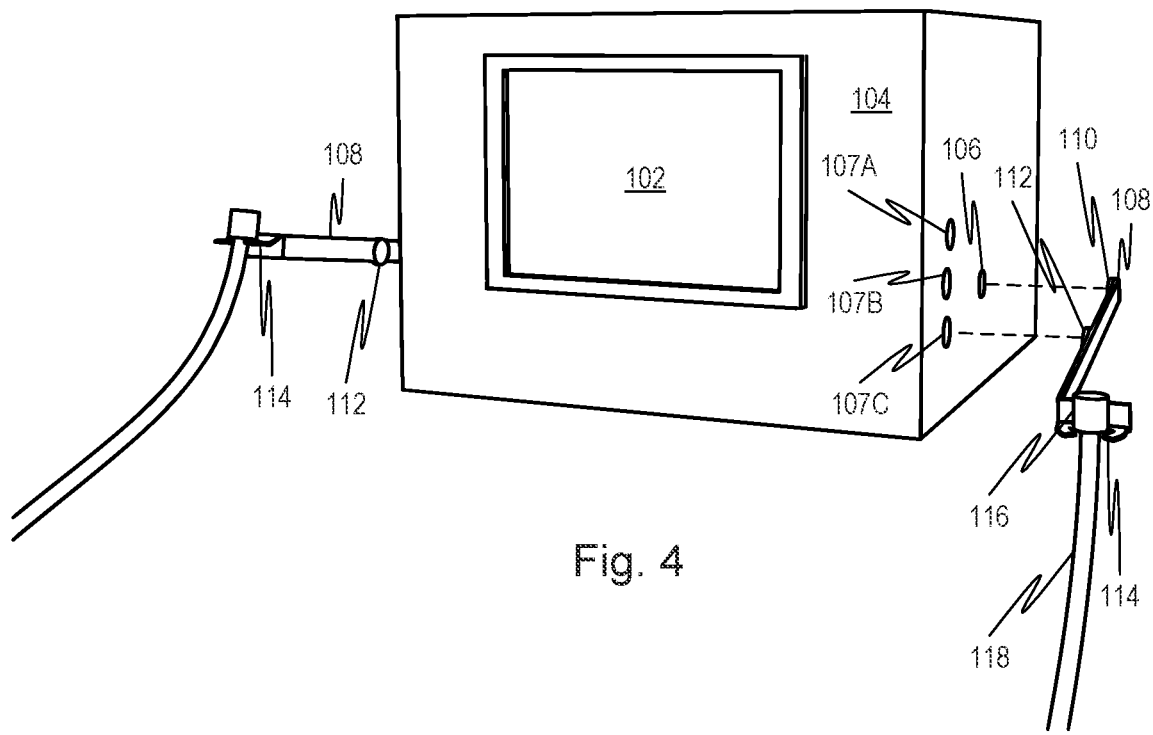
FIG. 4 shows alignment of a mount with magnets on a treatment machine housing according to embodiments of the disclosed subject matter.

FIGS. 3A and 3B show the treatment machine housing 104 with mounts 114 ready to attach to the housing 104 (left side of FIG. 3A) and attached (right side of FIG. 3A), respectively, according to embodiments of the disclosed subject matter. Referring now also to FIG. 4, it shows alignment of a mount 114 with magnets (also referred to as ferromagnetic elements) 107A, 107B and 107C on the treatment machine housing 104.

The housing 104 has an integral display 102. The details of the housing 104 are not specific to the invention and are shown by way of example, only. Magnets or ferromagnetic elements are shown at 106 and 107A-107C. The magnets or ferromagnetic elements attract magnets or ferromagnetic elements 110 and 112 of a line holder 108 that carries the mount 114 at its end. When the line holder 108 is brought in contact and aligned so that magnets 110 and 112 are aligned with respective ones of the magnets or ferromagnetic elements 106 and 107A-107C, the line holder 108 is held in position on the side of the housing 104 thereby positioning the mount 114 in a convenient location for use as a third hand for the management and organization of fluid lines during use of the treatment machine. That is, a treatment line 118 with a connector 116 can be positioned in the mount 114 which may be shaped to engage and hold the connector 116, for example, as shown in FIG. 2B. In FIG. 2A the treatment line 118 and mount 114 are shown separated and ready to be engaged.

FIG. 3A shows the line holder 108 in position and orientation ready to be engaged with the magnets or ferromagnetic elements shown at 106 and 107A-107C on either side of the housing 104 and prior to attachment. The user may choose combination of the magnet or ferromagnet element among 107A, 107B, and 107C such that the line holder 108 is held at a selected angle. FIG. 3B shows the line holder 108 attached to the housing 104 by means of the magnets or ferromagnetic elements 106 and 107B such that the mount 114 is held straight out and approximately horizontal. By selecting the magnet or ferromagnetic element 107B and thereby orienting the line holder 108, the mount 114 is placed at a predefined position relative to the housing 104. The position and orientation may be changed by selecting magnet or ferromagnetic element 106 with either 107A or 107C as can be confirmed by observation of FIG. 4, where the line holder 108 is aligned with that pair of magnets or ferromagnetic elements on the other side of the housing 104. This lowers the position of the mount 114. If the magnets or ferromagnetic elements 110 and 112 of a line holder 108 are aligned with the magnets or ferromagnetic element 106 in combination with magnets or ferromagnetic elements 107A, the position of the mount 114 is higher. This allows a user to select a vertical position of the mount 114 for convenience. In addition, a user is able to select the side of the housing 104 on which to position the line holder 108 and thereby position the mount 114.

Note that one of each complementary pair of a magnet or ferromagnetic element may be used. Examples of ferromagnetic elements are iron or steel. Magnets or ferromagnetic elements 106 and 107A, 107B, and 107C may be attached inside the housing 104 so that the side of the housing remains smooth. In embodiments, the housing may bear markings or indentations to indicate where the magnets or ferromagnetic elements 106 and 107A, 107B, and 107C are located in order to facilitate the attachment of the magnets or ferromagnetic elements 110 and 112 of the line holder 108.

Figure 5:
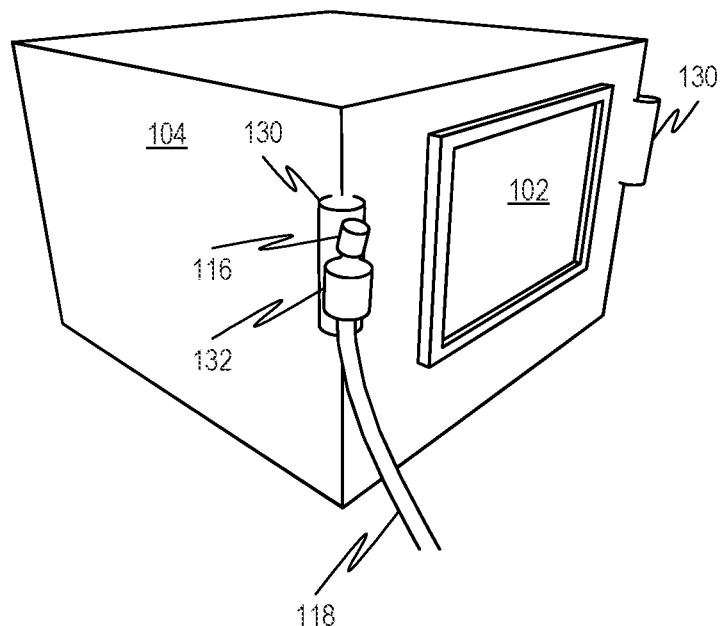
FIG. 5 shows a mounting system employing magnets according to embodiments of the disclosed subject matter.

FIG. 5 shows a mounting system employing magnets according to embodiments of the disclosed subject matter. A magnet or ferromagnetic element 132 is provided on a fluid line having a connector 116. A magnet or ferromagnetic element 130 is also provided at two positions on the housing 104. The fluid line 118 may thereby be attached to the housing 104 conveniently.

Figure 6:
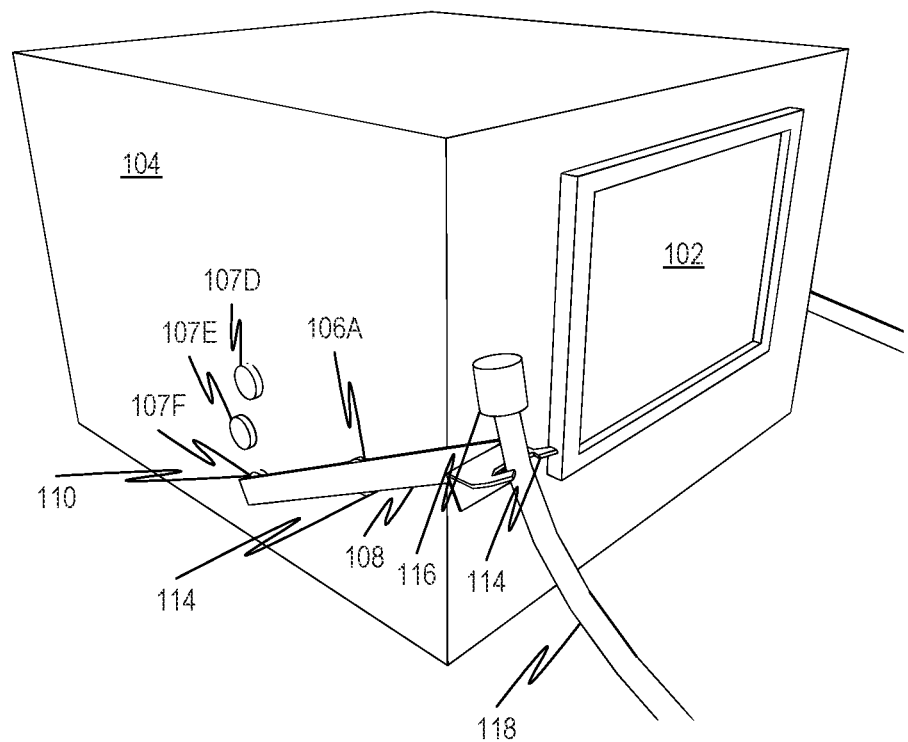
FIG. 6 shows another mounting system employing magnets according to embodiments of the disclosed subject matter.

FIG. 6 shows another variation of the embodiment of FIG. 3A. In the present case, the magnets that permit the angle of the line holder 108 to be selected are arrayed toward the rear end of the housing 104. The ferromagnetic element 106A, which may be a magnet or ferromagnetic element, may be supported on a boss or recessed with a protruding complementary magnet or ferromagnetic element on the line holder 108 facing it and engaging it. The presence of the recess or boss makes the line holder support positively and interferingly engage with the housing thereby making the connection more secure than if the surface were smooth and relied entirely on magnetic attraction. FIG. 6 also shows the line holder 108 in position and orientation ready to be engaged with the magnets or ferromagnetic elements shown at 106 and 107A-107C on either side of the housing 104 and prior to attachment. The user may choose combination of the magnet or ferromagnet element among 107D, 107E, and 107F such that the line holder 108 is held at a selected angle. Note that the 116 engages with the flexible tube 118 without relying on the connector 116 at the end of the tube 118. That is the gap in the mount 114 is tight enough to grip the tube 118. This leaves the connector free for removal of a cap and connection of a mating connector.

In the present disclosure, elements are identified as either magnets or ferromagnetic elements. Since magnets can be attracted to other magnets or to ferromagnetic elements, it should be evident that a complementary pair of a ferromagnetic elements with a magnet or a pair of magnets may produce the functional arrangement described herein.

Note that in the described embodiments, the magnets or ferromagnetic elements 106 and 107A-017C can be mounted inside a plastic housing 104 so they are not visible from the outside. Note also that pairs of magnets or ferromagnetic elements can be positioned in a variety of locations on the housing 104 to allow a variety of positions and orientations of the line holder 108 and mount 114.

Figure 7:
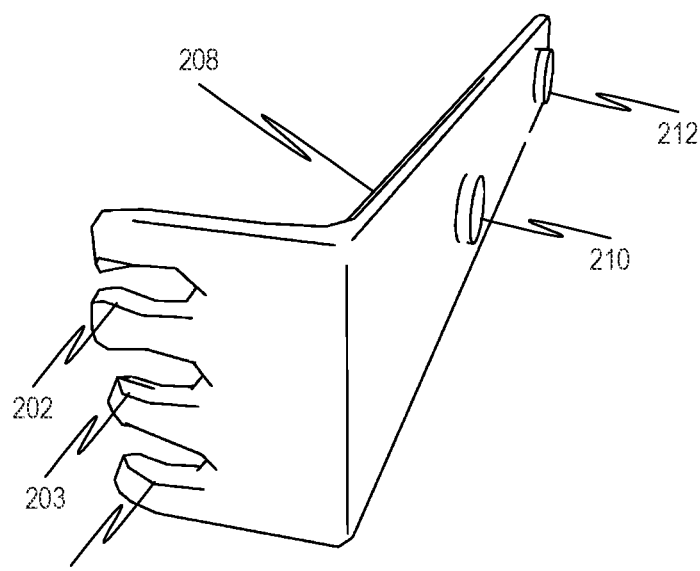
FIG. 7 shows another form of mount having multiple slots for holding tubes according to embodiments of the disclosed subject matter.

FIG. 7 shows another form of mount having multiple slots for holding tubes, according to embodiments of the disclosed subject matter. A line holder 208 has three slots 202, 203, and 204 providing the ability to hold multiple lines or to position the line in various positions. The line holder 208 is in other respects the same as line holder 108 of the previous embodiments. The line holder 208 has magnets or ferromagnetic elements at 212 and 210 which can be attached at any pair of magnets or ferromagnetic elements that include 106A (FIG. 6), which may be paired with 107D, 107E, or 107F to position the line holder 208 at various angles and positions.

Figure 8:
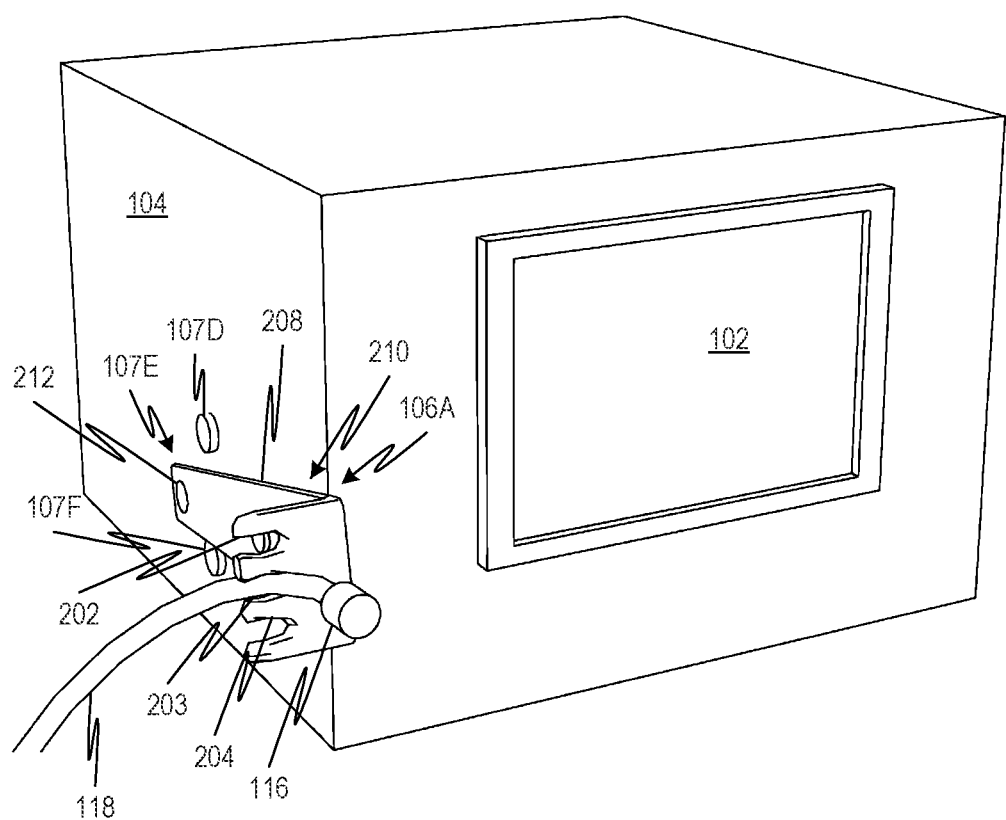
FIG. 8 shows the mount of FIG. 7 attached to a treatment machine housing according to embodiments of the disclosed subject matter.

FIG. 8 shows the line holder 208 of FIG. 7 mounted on a treatment machine housing 104. The line holder 208 is paired with magnets or ferromagnetic elements 107E and 106A. In the drawing of FIG. 8, magnets or ferromagnetic elements at 212 and 210 of the line holder 208 are paired with the magnets or ferromagnetic elements at 107E and 106A. Slot 203 holds the line 118 with a slight grip so that the connector 116 extends somewhat away from the line holder 208 toward the front of the machine housing 104. The line 118 can be moved between the slots 202, 203, and 204. The line holder 208 may be tilted to different angles by choosing a different magnet or ferromagnetic element among 107D and 107F. As indicated above, the machine housing 104 may have an integrated display 102.

Note that although the drawings show magnets or ferromagnetic elements on the outside of the housing it will be understood that they can be mounted within the housing so that they are not visible. Also, the housing may have bosses or recess located where the magnets or ferromagnetic elements attach such that there is a positive engagement between the ones on the line holder and the housing. Sole or complementary bosses and recesses may be positioned on the housing, the holder, both, or either.

Note that in FIG. 1, the array of magnets or ferromagnetic elements are spread out toward the rear of the housing and in FIG. 6 they are spread out toward the front of the housing. It should be clear to the reader that the ability to select an angle for the line holder 108 may be provided in either fashion and either one may be used with any of the disclosed embodiments.

According to embodiments, the disclosed subject matter includes a line mount with a treatment machine housing having one or more magnets or ferromagnetic elements mounted thereon. A line holder has at least one complementary one of magnets and ferromagnetic elements such as to cause the line holder to attached magnetically to the housing. The one or more magnets or ferromagnetic elements are numbered and arranged to permit the line holder to be supported thereby in multiple positions and orientations relative to the housing.

According to first embodiments, the disclosed subject matter includes a line mount on a treatment machine housing having one or more magnets or ferromagnetic elements mounted thereon. A line holder has at least one complementary one of magnets and ferromagnetic elements such as to cause the line holder to be attachable magnetically to the housing. The one or more magnets or ferromagnetic elements are numbered and arranged to permit the line holder to be supported thereby in multiple positions and orientations relative to the housing.

The first embodiments may include ones in which the one or more is at least two and the line holder has a longitudinal aspect with an axis that runs between the at least two when supported by the housing.

The first embodiments may include ones in which the line holder is a longitudinal member with a mount shaped to engage a fluid line.

The first embodiments may include ones in which the line holder is a longitudinal member with a mount shaped to engage a fluid line of a connector of a fluid line.

According to second embodiments, the disclosed subject matter includes a line mount system for a treatment machine housing having one or more magnets or ferromagnetic elements mounted thereon. A line holder has at least one complementary one of magnets and ferromagnetic elements such as to cause the line holder to be attachable magnetically to the housing.

The second embodiments may include ones in which the one or more magnets or ferromagnetic elements is at least two magnets or ferromagnetic elements on either side of the treatment machine housing.

The second embodiments may include ones in which the line holder has multiple slots for receiving flexible lines.

The second embodiments may include ones in which the housing has a boss or a recess onto or into which one of the ferromagnetic elements of the line holder fits.

According to third embodiments the disclosed subject matter includes a method of supporting a line. The method includes providing a treatment machine housing having one or more magnets or ferromagnetic elements mounted thereon. The method includes providing a line holder having at least one complementary one of magnets and ferromagnetic elements such as to cause the line holder to be attachable magnetically to the housing. The one or more magnets or ferromagnetic elements are numbered and arranged to permit the line holder to be supported thereby in multiple positions and orientations relative to the housing. The method includes moving the line holder from one side of the treatment machine housing, selecting a position of the line holder and attaching the line holder to the housing such that it is held in position by magnetic attraction.

The third embodiments may include ones in which the one or more is at least two and the line holder has a longitudinal aspect with an axis that runs between the at least two when supported by the housing.

The third embodiments may include ones in which the line holder is a longitudinal member with a mount shaped to engage a fluid line.

The third embodiments may include ones in which the line holder is a longitudinal member with a mount shaped to engage a connector of a fluid line.

According to fourth embodiments, the disclosed subject matter includes a method supporting a medical treatment fluid line. The method includes providing a treatment machine housing having one or more magnets or ferromagnetic elements mounted thereon. The method includes providing a line holder having at least one complementary one of magnets and ferromagnetic elements such as to cause the line holder to be attachable magnetically to the housing. The method includes moving the line holder from one side of the treatment machine housing and selecting a position of the line holder and attaching the line holder to the housing such that it is held in position by magnetic attraction.

The fourth embodiments may include ones in which the one or more magnets or ferromagnetic elements is at least two magnets or ferromagnetic elements on either side of the treatment machine housing.

The fourth embodiments may include ones in which the line holder has multiple slots for receiving flexible lines.

The fourth embodiments may include ones in which the housing has a boss or a recess onto or into which one of the ferromagnetic elements of the line holder fits.

According to fifth embodiments, the disclosed subject matter includes a line mount with a treatment machine housing having one or more magnets or ferromagnetic elements mounted thereon. A line holder has at least one complementary one of magnets and ferromagnetic elements such as to cause the line holder to be attachable magnetically to the housing. The housing or the line holder has a boss or a recess and the line holder having the other of a boss or recess such that the boss fits into the recess when the line holder is attached to the housing.

The fifth embodiments may include ones in which the line holder has multiple slots at different positions allowing a tube to be connected at various vertical points.

The fifth embodiments may include ones in which the boss is a magnet.

The fifth embodiments may include ones in which the one or more magnets or ferromagnetic elements is at least two magnets or ferromagnetic elements on either side of the treatment machine housing.

The fifth embodiments may include ones in which the line holder has multiple slots for receiving flexible lines.

The fifth embodiments may include ones in which the housing has a boss or a recess onto or into which one of the ferromagnetic elements of the line holder fits.

In any of the foregoing embodiments, the line holder may have multiple slots.

In any of the foregoing embodiments, the line holder may have multiple slots adapted for holding a line in a position so that it points away from the front of the machine toward a user.

In variations of the mount, the one or more is at least two and the line holder has a longitudinal aspect with an axis that runs between the at least two when supported by the housing. In further variations, the line holder is a longitudinal member with a mount shaped to engage the connector of a fluid line.

It is, thus, apparent that there is provided, in accordance with the present disclosure, a line holder. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

What is claimed is:

1. A fluid line mount system, comprising:
a medical treatment machine having a housing, the housing having an outer surface and a plurality of first magnets or ferromagnetic elements directly mounted to the outer surface of the housing; and
a line holder having at least two complementary magnets or ferromagnetic elements such that the line holder is attachable magnetically to the housing when the at least two complementary magnets or ferromagnetic elements come into contact with at least two of the plurality of the first magnets or ferromagnetic elements; and, wherein the plurality of the first magnets or ferromagnetic elements includes at least three magnets or ferromagnetic elements, and the at least three magnets or ferromagnetic elements have positions that enable the line holder to be magnetically attached to the housing in multiple positions and orientations relative to the housing, each of the multiple positions and orientations corresponding to a respective pair of the first magnets or ferromagnetic elements.

2. The line mount system of claim 1, wherein the line holder has a longitudinal aspect with an axis that runs between two of the at least three magnets or ferromagnetic elements when the line holder is magnetically attached to the housing.

3. The line mount system of claim 1, wherein the line holder is a longitudinal member with a mount shaped to engage a fluid line.

4. The line mount system of claim 1, wherein the line holder is a longitudinal member with a mount shaped to engage a connector of a fluid line.

5. The line mount system of claim 1, wherein the line holder has multiple slots for receiving multiple fluid lines.

6. The line mount system of claim 1, wherein the housing has a recess into which one of the at least two complementary magnets or ferromagnetic elements of the line holder fits.

7. The line mount system according to claim 1, wherein an outermost surface of each of the first magnets or ferromagnetic elements is flush with the outer surface of the housing, resulting in a combined surface that is smooth.

8. The line mount system of claim 1, wherein the outer surface of the housing has a boss onto which one of the at least two complementary magnets or ferromagnetic elements of the line holder fits.

9. A method of using a medical treatment device that supports a fluid line, the method comprising:
providing the medical treatment device, the medical treatment device having a housing that includes a plurality of first magnets or ferromagnetic elements directly mounted on an outer surface of the housing, the plurality including at least three magnets or ferromagnetic elements;
providing a line holder having at least two complementary magnets or ferromagnetic elements such that the line holder is attachable magnetically to the housing when the at least two complementary magnets or ferromagnetic elements come into contact with at least two of the plurality of the first magnets or ferromagnetic elements;
removing the line holder from a first position on the housing, the first position corresponding to the line holder being held by a first pair of the first magnets or ferromagnetic elements; and
attaching the line holder to a second position on the housing, the second position corresponding to a second pair of the first magnets of ferromagnetic elements, different from the first pair, such that the line holder is held in the second position by magnetic attraction between the at least two complementary magnets or ferromagnetic elements and the second pair of the plurality of the first magnets or ferromagnetic elements.

10. The method of claim 9, wherein the line holder has a longitudinal aspect with an axis that runs between at least two of the first magnets or ferromagnetic elements when the line holder is supported by the housing.

11. The method of claim 9, wherein the line holder is a longitudinal member with a mount shaped to engage a fluid line.

12. The method of claim 9, wherein the line holder is a longitudinal member with a mount shaped to engage a connector of a fluid line.

13. A method of supporting a medical treatment fluid line of a medical treatment machine, comprising:
providing the medical treatment machine, the medical treatment machine including a housing, the housing having a plurality of first magnets or ferromagnetic elements mounted on an outer surface of the housing, the plurality including at least three magnets or ferromagnetic elements;
providing a line holder having at least two complementary magnets or ferromagnetic elements such that the line holder is attachable magnetically to the housing when the at least two complementary magnets or ferromagnetic elements come into contact with at least two of the plurality of the first magnets or ferromagnetic elements; and
moving the line holder from a first position on the housing to a second position on the housing, the first position corresponding to a first pair of the first magnets or ferromagnetic elements and the second position corresponding to a second pair, different from the first pair, of the first magnets or ferromagnetic elements,
wherein the line holder is held in the first position by a magnetic attraction between the at least two complementary magnets or ferromagnetic elements and the first pair, and
the line holder is held in the second position by a magnetic attraction between the at least two complementary magnets or ferromagnetic elements and the second pair.

14. The method of claim 13, wherein the one or more plurality of the first magnets or ferromagnetic elements includes at least two magnets or ferromagnetic elements on a first face of the treatment machine housing.

15. The method of claim 13, wherein the line holder has multiple slots for receiving flexible lines.

16. The method of claim 13, wherein the housing has a boss or a recess onto or into which one of the at least two complementary magnets or ferromagnetic elements of the line holder fits.

* * * * *